US010660636B2

(12) United States Patent
Heneveld

(10) Patent No.: US 10,660,636 B2
(45) Date of Patent: *May 26, 2020

(54) SUTURE APPARATUS, SYSTEM AND METHOD

(71) Applicant: SUTURE EASE, INC., San Jose, CA (US)

(72) Inventor: Scott Heneveld, Whitmore, CA (US)

(73) Assignee: SUTURE EASE, INC., San Jose, CA (US)

( * ) Notice: Subject to any disclaimer, the term of this patent is extended or adjusted under 35 U.S.C. 154(b) by 235 days.

This patent is subject to a terminal disclaimer.

(21) Appl. No.: 15/695,632

(22) Filed: Sep. 5, 2017

(65) Prior Publication Data

US 2017/0367693 A1 Dec. 28, 2017

Related U.S. Application Data

(63) Continuation-in-part of application No. 14/847,905, filed on Sep. 8, 2015, now Pat. No. 10,231,730, which is a continuation-in-part of application No. 14/333,120, filed on Jul. 16, 2014, now Pat. No. 9,301,748.

(60) Provisional application No. 62/383,538, filed on Sep. 5, 2016, provisional application No. 62/048,239, filed on Sep. 9, 2014, provisional application No.
(Continued)

(51) Int. Cl.
*A61B 17/04* (2006.01)
*A61B 17/06* (2006.01)
*A61B 17/00* (2006.01)

(52) U.S. Cl.
CPC ...... *A61B 17/0485* (2013.01); *A61B 17/0469* (2013.01); *A61B 17/0483* (2013.01); *A61B 17/06066* (2013.01); *A61B 2017/00349* (2013.01); *A61B 2017/061* (2013.01); *A61B 2017/06042* (2013.01)

(58) Field of Classification Search
CPC ............ A61B 17/0485; A61B 17/0483; A61B 17/0469; A61B 2017/061; A61B 2017/06042; A61B 2017/00349
USPC .......................... 606/144, 145, 146, 205, 207
See application file for complete search history.

(56) References Cited

U.S. PATENT DOCUMENTS 5,817,111 A 10/1998 Riza
2014/0012292 A1* 1/2014 Stewart .............. A61B 17/0483
606/148

OTHER PUBLICATIONS

Office Action dated Dec. 29, 2017 from related U.S. Appl. No. 14/847,905.

* cited by examiner

*Primary Examiner* — Vy Q Bui
(74) *Attorney, Agent, or Firm* — Innovation Capital Law Group, LLP; Vic Lin

(57) ABSTRACT

A suture apparatus having a housing, actuator and capture rod, the actuator being engaged to the capture rod to form an actuator-capture rod assembly, an elongated cannula shaft having a lumen that extends through the shaft, and capture rod retraction means, the housing including an internal region that is configured to receive and support the capture rod retraction means, actuator proximal end and actuator rod distal end therein, wherein said capture rod retraction means is in communication with said actuator. The actuator-capture rod assembly and capture rod retraction means being positioned and configured to transition from a retracted position
(Continued)

to an extended position when an actuation force is applied to the actuator and return the retracted position by the retraction means when the actuation force is released.

17 Claims, 11 Drawing Sheets

Related U.S. Application Data

61/944,053, filed on Feb. 24, 2014, provisional application No. 61/846,899, filed on Jul. 16, 2013.

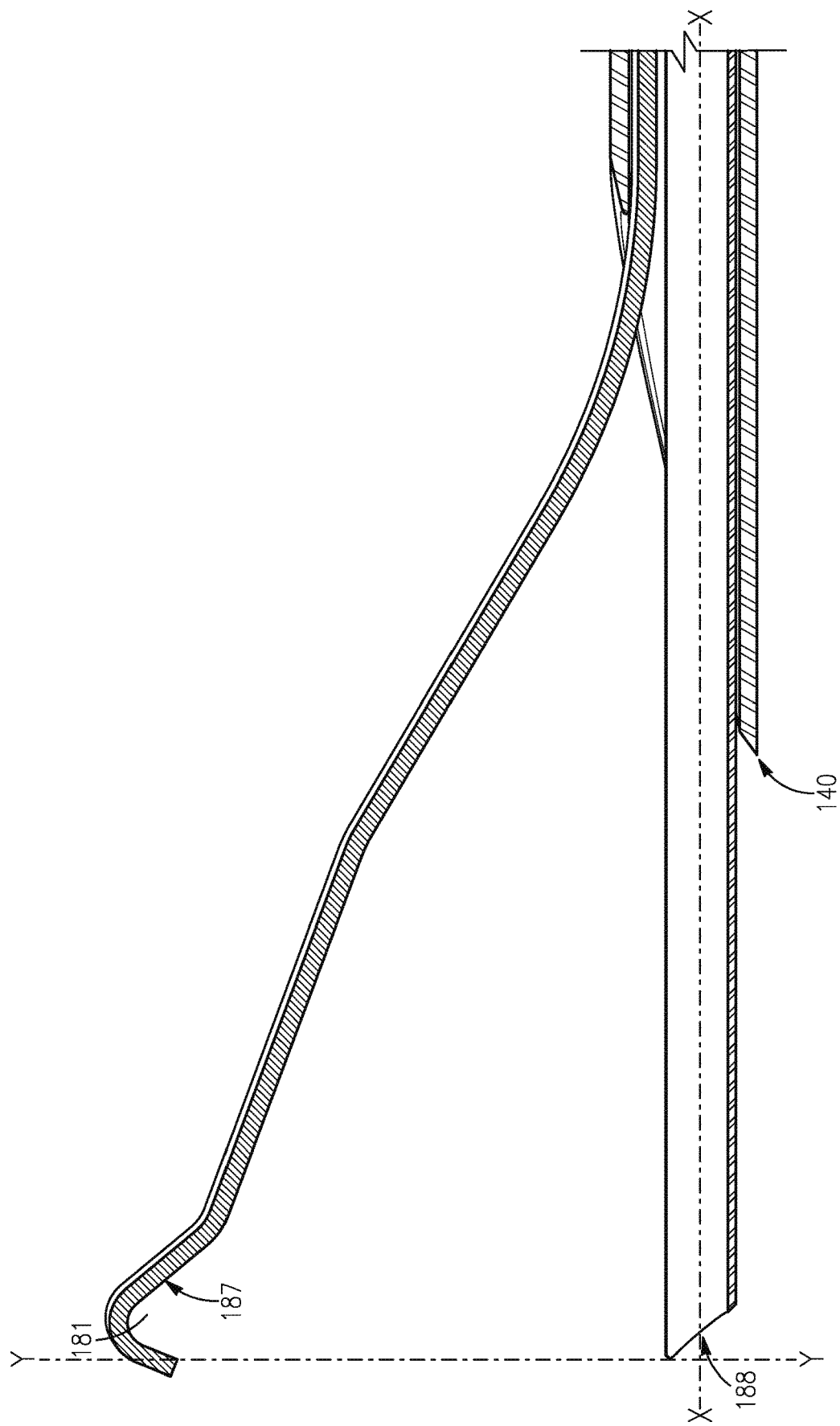

SUTURE APPARATUS, SYSTEM AND METHOD

CROSS-REFERENCE TO RELATED APPLICATIONS

This application claims benefit of priority to U.S. Provisional Application Ser. No. 62/383,538, filed Sep. 5, 2016. This application also is a continuation-in-part of U.S. Non-Provisional patent application Ser. No. 14/847,905, filed Sep. 8, 2015, claims the benefit of priority of U.S. Provisional Patent Application Ser. No. 62/048,239, filed on Sep. 9, 2014, and is a continuation-in-part of U.S. Non-Provisional patent application Ser. No. 14/333,120 filed on Jul. 16, 2014, now, U.S. Pat. No. 9,301,748, which claims priority to U.S. Provisional Patent Application Ser. Nos. 61/846,899 filed on Jul. 16, 2013 and 61/944,053, filed on Feb. 24, 2014. Each application recited above is herein fully incorporated by reference herein.

FIELD OF THE INVENTION

The present invention relates to surgical instruments for approximation, ligation and fixation of tissue using a suture, and particularly to the approximation of tissue separated by mean of an endosurgical trocar being inserted into a body cavity.

BACKGROUND OF THE INVENTION

Numerous methods currently exist for performing laparoscopic procedures. One of the more common used methods is known as closed laparoscopy, which utilizes a sharp needle (e.g., Veress needle) to puncture the abdominal wall and insufflate the abdominal cavity with an inert gas, such as carbon dioxide, through the needle. The noted process of insufflating the cavity separates the abdominal wall from the underlying organs creating a gap for the surgeon to work within. A trocar/cannula system is then used to maintain the insufflated cavity and provide a working portal for which instruments can be passed into and out of the abdominal cavity to perform various surgical procedures.

When the laparoscopic procedure is completed, the surgeon must then close the incision site at the inner abdominal wall using suture material to minimize the risk of adverse post-operative events.

Various apparatus and methods have thus been developed and employed to approximate, ligate and fixate the tissue post a laparoscopic procedure. Illustrative are the apparatus and methods disclosed in U.S. Pat. Nos. 919,138, 3,946,740 and 4,621,640.

U.S. Pat. No. 919,138 discloses an approximation method comprising driving a hollow needle through the tissue with the suture material passing through the hollow center lumen. The needle is then withdrawn, leaving the suture material in place, and the suture is tied to complete the approximation.

There are several significant disadvantages and drawbacks associated with such apparatus and methods. A major drawback is that the apparatus and methods are configured and, hence, primarily employed for use in open surgical procedures where there is room for the surgeon to manipulate the instrument.

U.S. Pat. No. 3,946,740 discloses an approximation apparatus that resembles traditional forceps and an approximation method employing same. The approximation apparatus is configured to pinch tissue between opposing jaws and pass a needle from one jaw through the tissue to the other jaw, where grasping means pull the needle and suture material through the tissue.

There are also several significant disadvantages and drawbacks associated with such apparatus and methods. A major drawback is that the apparatus and methods are similarly configured and, hence, primarily employed for use in open surgical procedures where there is room for the surgeon to manipulate the instrument.

Various apparatus and methods have also been developed to approximate, ligate and fixate tissue post a laparoscopic procedure performed via endoscopic surgery. As is well known in the art, a laparoscopic procedure performed via endoscopic surgery often comprises inserting small tubes called trocars into the body cavity. The tubes typically have a diameter between 3-30 mm and a length of about 150 mm (6 inches).

Illustrative apparatus and methods to approximate tissue post a laparoscopic procedure performed via endoscopic surgery are disclosed in U.S. Pat. Nos. 4,621,640 and 4,935,027.

There are several significant disadvantages and drawbacks associated with the apparatus and methods disclosed in the noted patents. A major drawback is that the apparatus are not configured to retrieve the needle from the body cavity. A further drawback is that the arc through which the needles must be driven into tissue is perpendicular to the axis of the device.

More recently, the approximation procedure employed by many surgeons comprises employing a semi-circular needle, attached to and carrying a suture, in a pair of endoscopic needle holders. An illustrative apparatus is disclosed in WO 2012/122129 A1.

The needle holders, which resemble a pair of pliers with an elongated shaft between the handles and the jaws, must be placed down through one of the surgical trocars into the body cavity containing the structure to be sutured.

Because of their size, the needles used in these procedures are generally not able to be held in the jaws of the needle driver while being introduced through the operative trocar. The surgeon must hold the suture in the needle holder jaws, and push the needle holder trailing the needle and suture into the body cavity.

A further drawback of the noted procedure is that the suture and needle combination is dropped in the body cavity, and the needle is then located and picked up and properly positioned in the needle holder jaws. This is a difficult and time-consuming aspect of the current endoscopic technique for suturing.

The needle carrying the suture must also be driven by pronation of the wrist, causing rotation of the elongate shaft, and subsequent arcuate rotation of the semi-circular needle.

A further drawback and limitation of this type of needle driver is that the needle may only be driven or rotated in a plane perpendicular to the axis of rotation; such axis being defined by the elongate shaft and the position of the surgical trocar. The current endoscopic needle drivers will thus not allow the surgeon to rotate the needle in an arc parallel to the trocar's axis. This is a significant limitation when attempting to ligate vessels, ligaments and other structures that run perpendicular to the axis of the operative trocar.

A further limitation of most current approximation apparatus and associated methods is that, if the surgeon desires to place more than one suture throw through the tissue, he/she must reload the needle into the needle driver. This may be done extracorporeally, i.e. outside the body, in a manner similar to the initial loading of the suture device, or it may be done intracorporeally, i.e. inside the body. This process is a time consuming, and oftentimes is a frustrating exercise in hand to eye coordination.

It is thus desirable to provide an improved suture apparatus and method that substantially reduces or eliminates the disadvantages and drawbacks associated with prior known suture apparatus and methods.

It is therefore an object of the present invention to provide novel suture apparatus and associated methods that substantially reduce or overcome the disadvantages and drawbacks associated with prior known suture apparatus and methods in a simple and economical manner.

It is a further object of the present invention to provide suture apparatus and methods that can be used in conjunction with modern day endoscopic surgical techniques.

SUMMARY OF THE INVENTION

The present invention is directed to suture apparatus, systems and associated methods for approximation, ligation and fixation of tissue; particularly, approximation of tissue separated by mean of an endosurgical trocar.

In some embodiments of the invention, the suture apparatus includes a handle comprising a housing, an actuator, a capture rod, the actuator being engaged to the capture rod to form an actuator-capture rod assembly, an elongated cannula shaft having a lumen therein, and capture rod retraction means for retracting the actuator-capture rod assembly from an extended position to a retracted position, the housing including an internal region that is configured to receive and support the capture rod retraction means, actuator distal end and actuator rod proximal end therein, wherein said capture rod retraction means is in communication with said actuator.

In a preferred embodiment, the actuator rod distal end includes suture capture means for capturing and seating a suture thereon.

In a preferred embodiment, the actuator-capture rod assembly and capture rod retraction means are positioned in the housing interior region, wherein, when an actuation force is applied to said actuator, the actuator-capture rod assembly transitions from the retracted position to the extended position, wherein the suture capture means extends out of the cannula shaft lumen, wherein the suture capture means is in a position to capture and seat a suture and, when a suture is seated in the suture capture means, release and eject the suture therefrom, and wherein, when the actuation force is released, the capture rod retraction means exerts a retraction force on the actuator-capture rod assembly to transition the actuator-capture rod assembly back to the retracted position.

In a preferred embodiment, when the suture capture means captures and seats a suture thereon and the actuator-capture rod assembly transitions to the retracted position, the suture is withdrawn into the cannula lumen.

In some embodiments of the invention, the suture capture means comprises a suture trough.

In some embodiments of the invention, the suture capture means comprises a wire tong member.

In some embodiments of the invention, the suture capture means comprises a wire tong member functioning in cooperation with a ground cannula with a formed tip to enhance capture of suture.

As set forth in detail herein, the present invention provides superior results and numerous advantages over prior art suture systems and methods. One significant advantage of the present invention is that the suture apparatus can be effectively employed to approximate tissue in conjunction with endoscopic surgery procedures.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 11D is a partial sectional perspective view of the capture finger and ejection sleeve in a fully extended state in accordance with the invention.

DETAILED DESCRIPTION OF THE PREFERRED EMBODIMENTS

Before describing embodiments of the present invention in detail, it is to be understood that this invention is not limited to particularly exemplified apparatus, systems and methods as such may, of course, vary. Thus, although a number of apparatus, systems, and methods similar or equivalent to those described herein can be used in the practice of the present invention, the preferred apparatus, systems and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise.

Definitions

The term "tissue", as used herein, means and includes mammalian biological tissue, such as, by way of example, human abdominal tissue.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with prior art suture apparatus and methods.

In overview, the present invention is directed to suture apparatus, systems and associated methods for approximation, ligation and fixation of tissue; particularly, approximation of tissue separated by means of an endosurgical trocar. The invention is, thus, particularly applicable with and for the trocar wound closure system disclosed in Applicant's Co-pending application Ser. No. 13/787,243.

Figure 1:
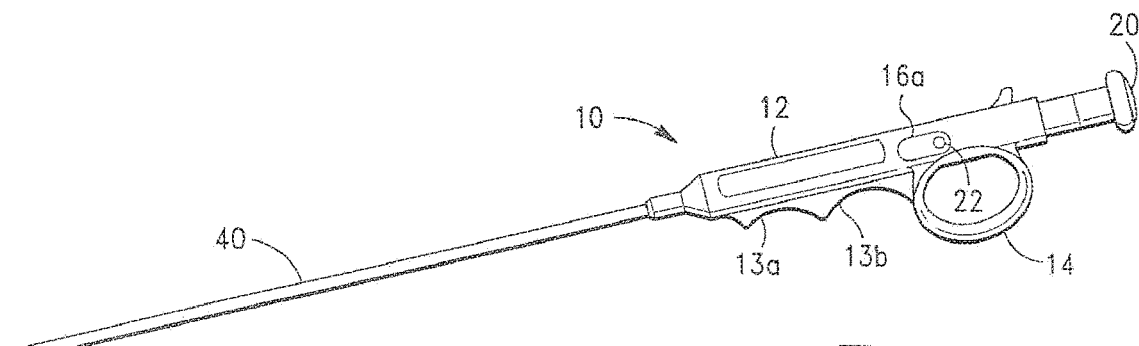
FIG. 1 is a perspective view of one embodiment of the suture apparatus, in accordance with the invention.
Figure 2A:
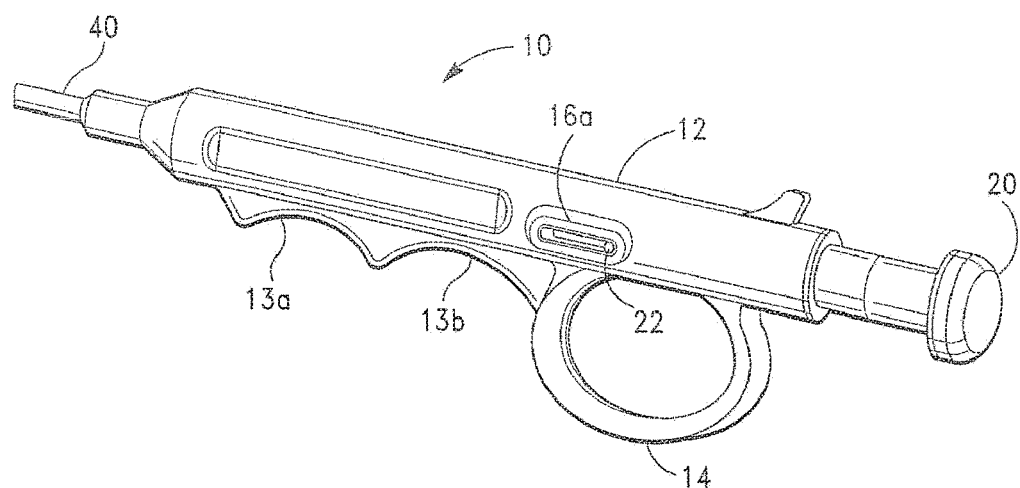
FIG. 2A is a partial perspective view of the suture apparatus shown in FIG. 1, showing the apparatus housing, in accordance with the invention.
Figure 2B:
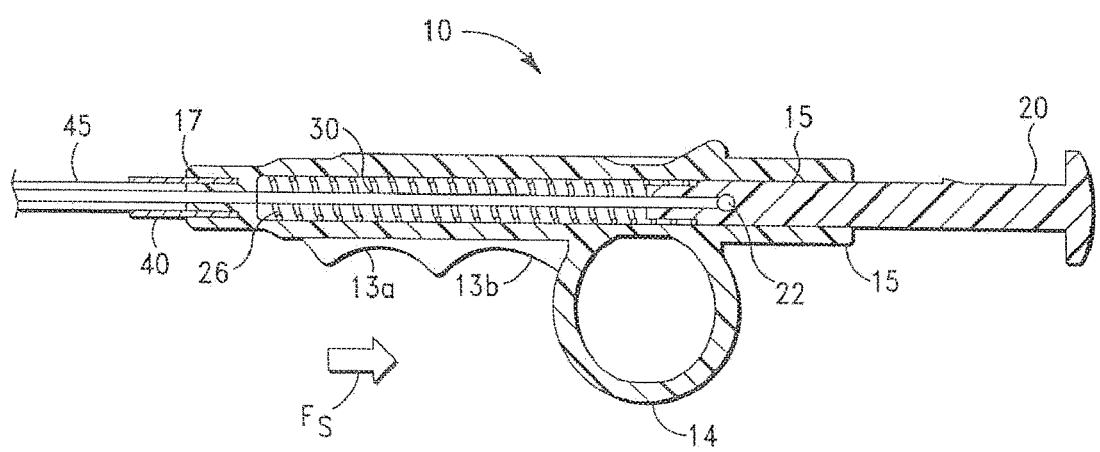
FIG. 2B is a partial perspective sectional view of the suture apparatus housing shown in FIG. 2A, in accordance with the invention.

Referring first to FIGS. 1, 2A and 2B, in a preferred embodiment of the invention, the suture apparatus 10 comprises a housing (or handle) 12, capture rod actuator 20, compression spring 26, capture rod 30 and tubular cannula shaft 40.

In a preferred embodiment, the apparatus 10 further includes a suture ejection sleeve or tube 45. As illustrated in FIG. 3D (and FIG. 5B), the suture ejection sleeve 45 is preferably disposed proximate the outer surface of the capture rod 30, more preferably, the suture ejection sleeve 45 is engaged or connected to the outer surface of the capture rod 30. Thus, in some embodiments, the capture rod 30 and suture ejection sleeve 45 comprises a press-fit configuration.

In some embodiments, the capture rod 30 and suture ejection sleeve 45 comprise an integral member, i.e. a capture rod with a stepped region proximate the distal end.

As discussed in detail below, the capture rod 30 includes suture capture means that is disposed on the distal end to capture and seat a suture thereon. In some embodiments of the invention, the suture capture means comprises a suture trough 32 (see FIG. 3B). In some embodiments, the suture capture means comprises a tong member 60 (see FIG. 5D)

In some embodiments, the housing 12 preferably includes at least one, more preferably, at least two (2) finger contours 13a, 13b and a finger ring 14 to facilitate a controlled grip and manipulation of the apparatus 10. As will be readily apparent to one having ordinary skill in the art, the housing 12 is configured to be used by the left or right hand without any degradation of apparatus control.

Figure 3A:
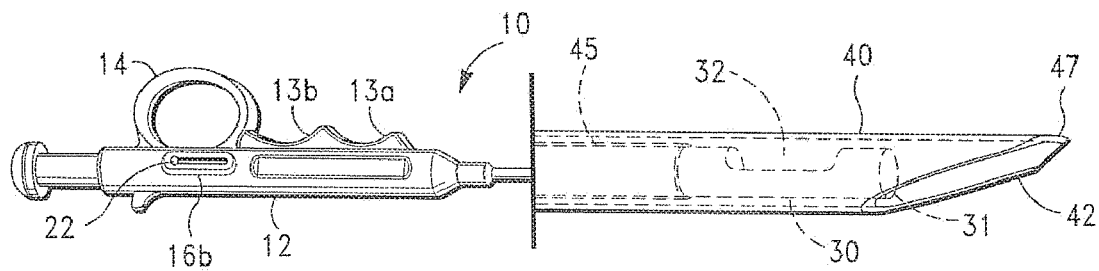
FIG. 3A is a partial sectional side plane view of the suture apparatus shown in FIG. 1, showing the apparatus housing, and one embodiment of a cannula and capture rod, in accordance with the invention.

As illustrated in FIGS. 2A and 3A, the housing 12 further comprises two parallel guide slots 16a, 16b, which are disposed adjacent to the finger ring 14. According to the invention, the guide slots 16a, 16b are positioned and configured to direct the travel of the capture rod actuator 20 via the capture rod actuator pin 22, which connects the capture rod actuator 20 to the capture rod 30.

According to the invention, the capture rod pin 22 can be configured whereby the pin 22 projects through each of the guide slots 16a, 16b or through one of the guide slots 16a, 16b. In some envisioned embodiments of the invention, not, shown, the housing 12 can comprise one guide slot, e.g. guide slot 16a.

Referring now to FIG. 2B, the interior of the housing 12 (denoted generally "15") is configured to contain and provide structural support for the compression spring 26, capture rod actuator 20 and capture rod 30. The distal end 17 of the housing 12 is further configured to secure the cannula 40 to the housing 12 (see FIG. 2B).

According to the invention, the compression spring 26 is positioned and configured to exert a spring force (denoted by arrow $F_s$) on the capture rod actuator 20 and, thereby, the actuator rod 30, when in a static state. In some embodiments, of the invention, the spring force $F_s$ is in the range of approximately 0.5-4 lbs. In a preferred embodiment, the spring force $F_s$ is approximately 2.5 lbs.

In a preferred embodiment, the capture rod actuator 20 is able to axially advance the capture rod 30 inside of the cannula tubular shaft 40 with minimal pressure applied via a surgeon's thumb. According to the invention, full thumb pressure can be exerted without concern that the capture rod 30 will over extend. After the thumb pressure is released, the capture rod actuator 20 returns to a spring loaded retracted position.

As illustrated in FIGS. 2A and 3A, in a preferred embodiment, the capture rod pin 22 is configured and aligned through the two parallel guide slots 16a, 16b in the housing 12. According to the invention, travel of the capture rod pin 22 and, hence, capture rod actuator 20 is controlled and limited by the guide slots 16a, 16b in the housing 12.

Referring now to FIGS. 3A-3D, the cannula 40 includes a beveled (and, preferably, sharp) edge 42 that is configured to pierce through tissue to facilitate suture passage. According to the invention, the edge 42 of cannula 40 can comprise various alternative shapes to facilitate piercing though tissue.

Figure 3B:
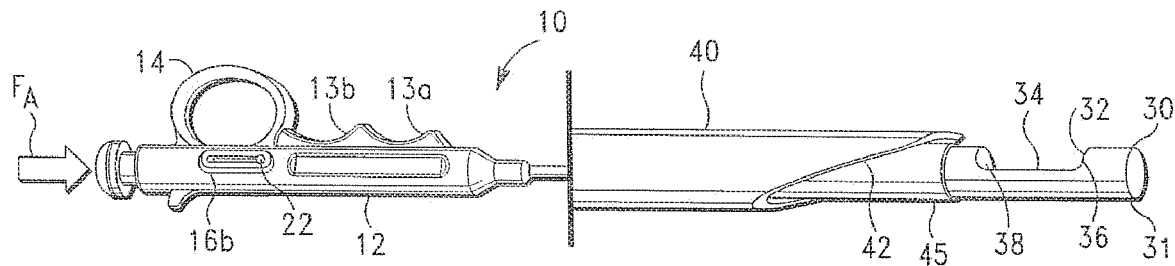
FIGS. 3B and 3C are side plane views of the suture apparatus shown in FIG. 3A, showing the apparatus housing, cannula and capture rod in an extended state, in accordance with the invention.
Figure 3C:
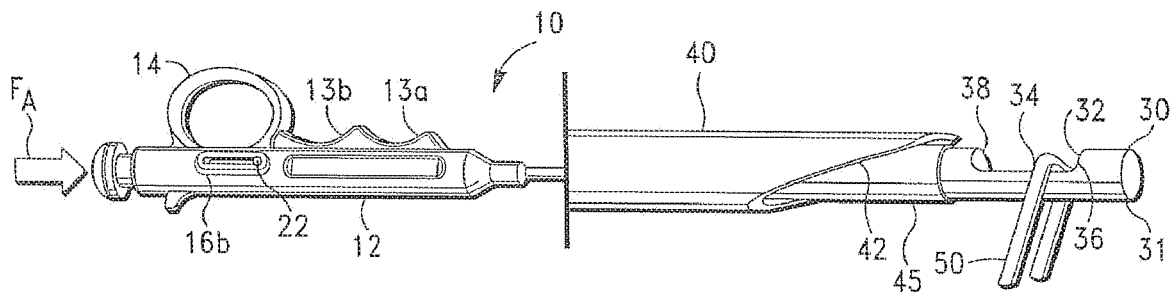
Figure 3D:
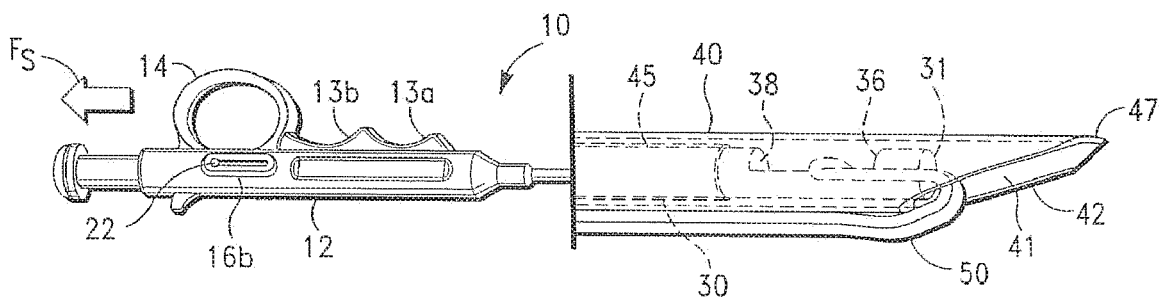
FIG. 3D is a partial sectional side plane view of the suture apparatus shown in FIG. 3C, showing the apparatus housing, cannula and capture rod with a suture seated thereon in a retracted state, in accordance with the invention.

To facilitate suture capture, the capture rod 30 is axially advanced from the static/retracted position shown in FIG. 3A to the extended position shown in FIGS. 3B and 3C by exerting an actuation force on the capture rod actuator 20 in the direction denoted by arrow $F_A$, wherein the distal end 31 of the capture rod 30 and, hence, suture capture means, in this embodiment, a suture trough 32, disposed thereon are exposed. As illustrated in FIG. 3C, a suture 50 can then be captured and seated in the suture trough 32 (and, as discussed below, release and eject the suture 50 when seated in the suture trough 32).

After the suture 50 is positioned in the suture trough 32, the capture rod actuator 20 is released, and the spring force $F_s$ exerted by the spring 26 withdraws the capture rod 30 with the suture 50 seated in the suture trough 32 into the cannula 40, as shown in FIG. 3D.

After subsequent or re-penetration of the tissue, the capture rod actuator 20 is actuated again (by applying the aforementioned actuation force), which advances the capture rod 30 back to the extended position (see FIG. 3C) to release and eject the suture 50 (or another engaged suture) from the capture rod 30.

As indicated above, in the illustrated embodiment, wherein the suture capture means comprises a trough 32, the suture apparatus 10 preferably includes an ejection sleeve 45 that is configured and positioned to facilitate the release and ejection of the suture 50 from the capture rod 30.

According to the invention, the suture trough 32 can comprise various configurations. In a preferred embodiment, the trough 32 includes a flat seat 34 and distal 36 and proximal 38 portions.

In some embodiments, the trough 32 proximal portion 38 has a substantially perpendicular or curvilinear configuration. An exemplar perpendicular configuration is shown in FIGS. 3A-3D.

Figure 4A:
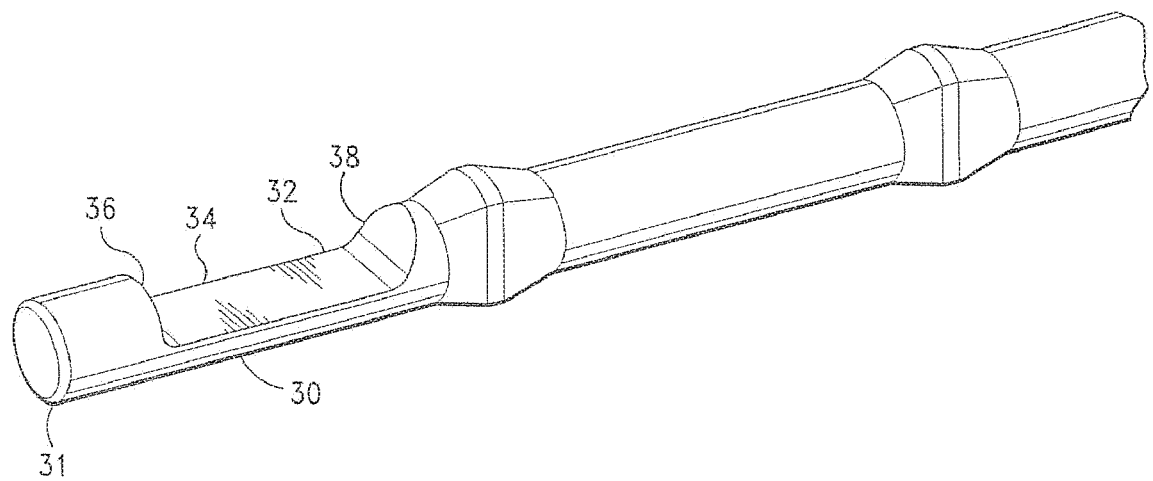
FIG. 4A is a partial perspective view of another embodiment of a capture rod, in accordance with the invention.
Figure 4B:
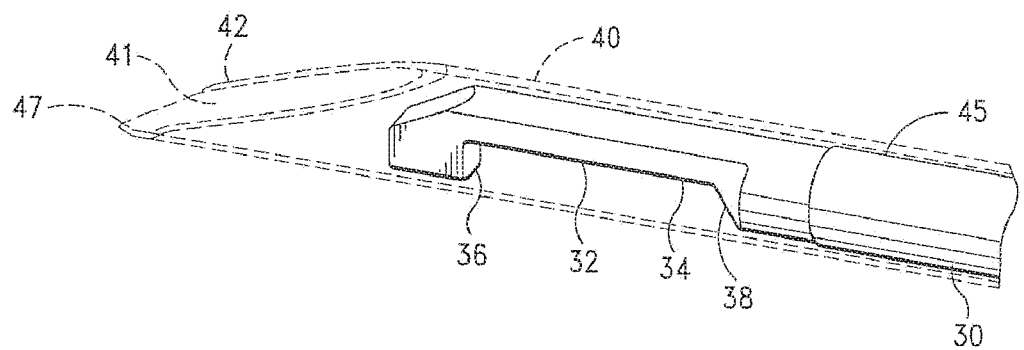
FIG. 4B is a partial sectional perspective view of the capture rod shown in FIG. 4A in a cannula lumen, in accordance with the invention.

In some embodiments, the trough 32 distal portion 36 has a substantially perpendicular or curvilinear configuration, such as shown in FIGS. 4A and 4B, to ensure suture retention during capture and withdrawal of the capture rod 30 into the cannula 40.

Figure 5A:
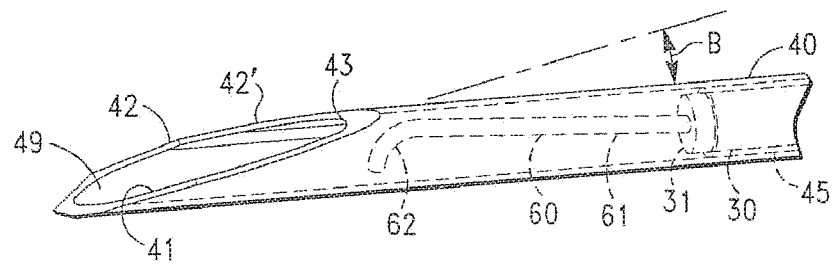
FIG. 5A is a partial sectional perspective view of the another embodiment of a capture rod having tong suture capture means, in accordance with the invention.
Figure 5B:
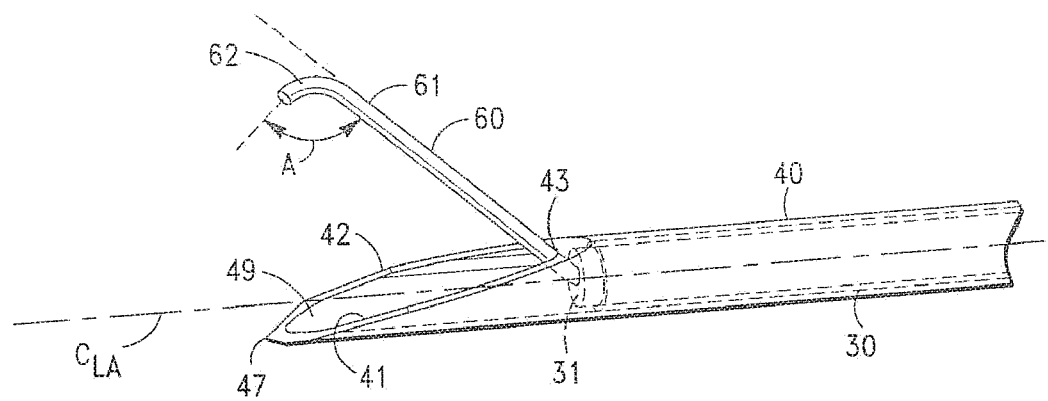
FIGS. 5B through 5D are partial perspective views of the capture rod shown in FIG. 5A, showing a cannula and capture rod in a first extended state, in accordance with the invention.
Figure 5C:
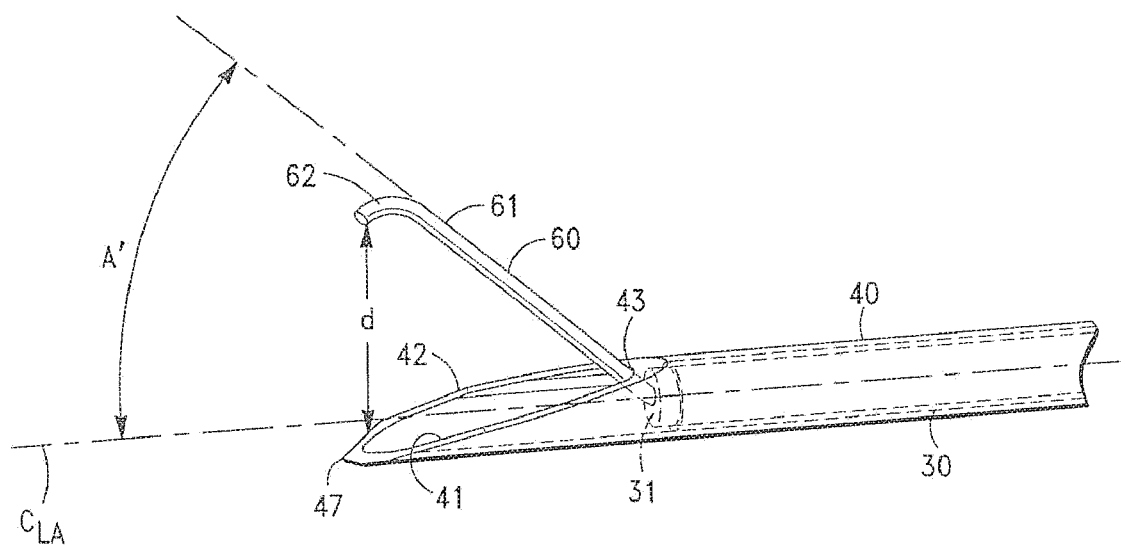

Referring now to FIGS. 5A-5F, another embodiment of suture capture means is shown. In the illustrated embodiment, the suture capture means comprises a flexible tong member 60. As illustrated in FIG. 5C, the tong member 60 is connected to the distal end 31 of the capture rod 30.

According to the invention, the tong member 60 can comprise various conventional materials. Thus, in some embodiments, the tong member 60 comprises a thin metal wire metal, such as a stainless steel wire. In some embodiments, the tong member 60 comprises a shape memory metal, such as Nitinol™.

As illustrated in FIGS. 5B and 5C, the tong member 60 includes an elongated portion 61 and a distal end 62 that is configured to capture a suture thereon. According to the invention, the tong member 60 can comprise various configurations, i.e. cross sections. In the embodiment illustrated in FIG. 5A-5F, the tong member comprises a substantially cylindrical member. In some embodiments, the tong member 60 has a rectangular cross section, whereby, as discussed below, the width of the ribbon tong member 60 provides optimum lateral clearance between the tong member 60 and the cannula 40.

According to the invention, the tong distal end 62 can also comprise various configurations to facilitate capturing and seating a suture thereon. In some embodiments of the invention, such as illustrated in FIG. 5B, the distal end 62 of the tong member 60 comprises a substantially linear region (or portion) that is configured to form an apex angle (denoted angle "A") with the elongated portion 61 (or longitudinal axis thereof). As discussed below, preferably apex angle A is less than approximately 90° to facilitate secure engagement of a suture on the tong member 60.

In some embodiments of the invention; particularly, wherein the tong member 60 comprises a rectangular or band member, the distal end 62 of the tong member 60 can also comprise a hook region or section that is bent to a critical configuration or angle that prevents a suture from slipping underneath hook section when one leg of the suture is being pulled on axially.

Referring now to FIGS. 5B and 5C, according to the invention, when the capture rod 30 is in a fully extended position or state, the elongated portion 61 of the tong member 60 and longitudinal axis of the cannula (denoted "$C_{LA}$") form an aperture angle (denoted angle "A'").

In some embodiments of the invention, the aperture angle A' is preferably in the range of approximately 30°-60° to facilitate the capture of a suture. In a preferred embodiment, the aperture angle A' is in the range of approximately 35°-45°.

As will readily be appreciated by one having ordinary skill in the art, the optimum apex angle A is less than 90°, whereby the interaction of the suture with the distal end 62 of the tong member 60 will drive the suture toward the apex to facilitate retention of the suture. When the apex angle is greater than 90°, the interaction of a suture with the distal end 62 of the tong member 60 will drive the suture away from the apex and allow inadvertent liberation of the suture.

As indicated above, the cannula 40 includes a beveled (and, preferably, sharp) edge 42 that is configured to pierce through tissue to facilitate suture passage. Referring to FIG. 5A, in some embodiments, the beveled cannula end 42' forms an angle with respect to the longitudinal axis of the cannula $C_{LA}$ (denoted angle "B") in the range of 12°-15°. In a preferred embodiment, the angle of the beveled cannula end is approximately 13°.

According to the invention, the noted aperture angle A' range and beveled cannula end 42' angle B range provide an optimum opening between the tong member 60 and the inner surface 49 of the cannula 40 and also facilitates secure engagement of a suture when seated on the tong member 60.

Referring to FIG. 5C, in some embodiments of the invention, opening between the tong member 60 and the inner surface 49 of the cannula 40 (denoted "d") is preferably in the range of approximately 0.200-0.400 in.

According to the invention, various lateral clearances between the tong member 60 and cannula inner surface 49 can be provided to accommodate various sized sutures. In some embodiments of the invention, the lateral clearance between each side of the tong member 60 and cannula inner surface 49 is preferably in the range of approximately 0.005-0.015 in. In a preferred embodiment the lateral clearance is approximately 0.010 in.

As illustrated in FIGS. 5B and 5C, when the capture rod 30 is in a fully extended position or state, the distal end 62 of the tong member 60 and tip 47 of the cannula 40 are also substantially aligned vertically to further enhance the engagement of a suture when seated on the tong member; particularly, when the capture rod 30 and, hence, tong member 30 is retracted into the cannula lumen 41.

According to the invention, various capture rod 30 lengths and/or travel thereof can be employed to provide various relationships (or orientations) by and between the distal end 62 of the tong member 60 and tip 47 of the cannula 40 when the capture rod 30 is in a fully extended position.

As illustrated in FIGS. 5B and 5C, in some embodiments, when the capture rod 30 is in a fully extended position, the distal edge 31 of the capture rod 30 is disposed proximate the inner edge 43 of the cannula 40.

Figure 5D:
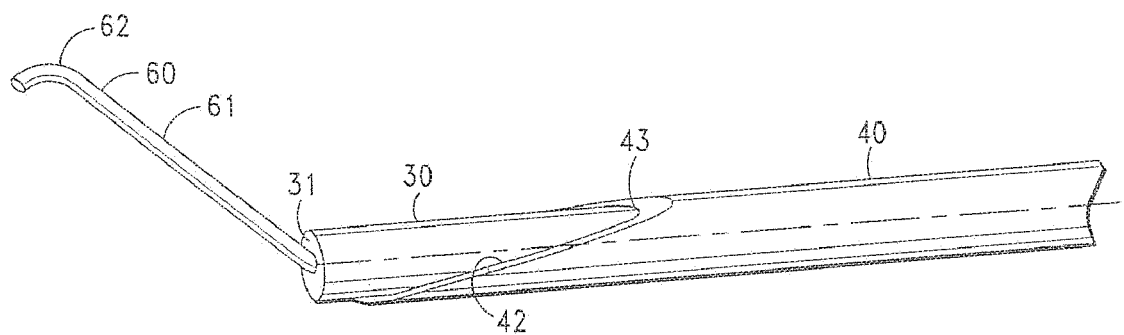
Figure 5E:
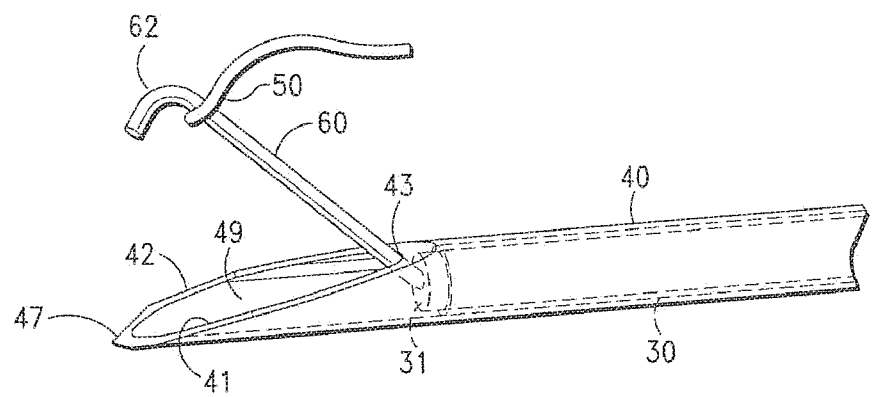
FIG. 5E is a further partial perspective view of the capture rod shown in FIG. 5A, showing a cannula and capture rod in a second extended state, in accordance with the invention.

As illustrated in FIG. 5D, in some embodiments, when the capture rod 30 is in a fully extended position, the distal edge 31 of the capture rod 30 extends beyond the tip of the cannula 47 to facilitate the release and ejection of a suture when seated thereon, i.e. the suture is easily released from the suture apparatus 10.

Referring now to FIG. 5A, the tong member 60 is configured to be seated in the cannula lumen 41 when in a static or pre-deployment configuration. In a preferred embodiment of the invention, the tong member 60 is configured or pre-shaped to transition from a restrained configuration when seated in the cannula lumen 41 to an expanded (or unrestrained) configuration when extending out of the cannula lumen 41 to provide the aforementioned optimum opening between the tong member 60 and the inner surface 49 of the cannula 40, such as shown in FIG. 5C, for capturing a suture 50.

Figure 5F:
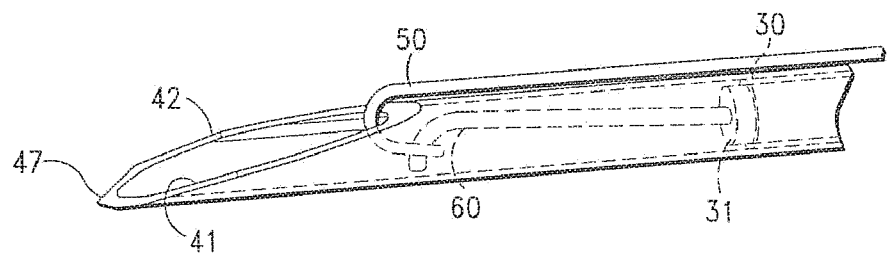
FIG. 5F is a partial sectional perspective view of the capture rod shown in FIG. 5D, showing the cannula and capture rod with a suture seated thereon in a retracted state, in accordance with the invention.

Upon retraction of the capture rod 30 and, hence, flexible tong member 60 attached thereto (by either a spring force or manual manipulation at the handle), the tong member 60 contacts and is deflected by the inner edge 43 of the cannula 40, forcing the tong member 60 down toward the open cannula surface 49, whereby a suture engagement force between the tong member 60 and open cannula surface 49 is provided that is sufficient to securely engage a captured suture between the tong member 60 and open cannula surface 49. Upon further retraction of the capture rod 30 and, hence, flexible tong member 60 attached thereto, the suture 50 is drawn into the cannula lumen 41, as shown in FIG. 5F.

A key feature and, hence, advantage of the invention is that the tong member 60 physical characteristics, e.g. modulus of elasticity and configuration, and the orientation of the tong member 60 and inner cannula surface 49 provides unrivaled suture retention capability. Indeed, in a preferred embodiment of the invention, a suture apparatus employing a tong member of the invention is capable of providing suture engagement forces that are substantially similar to the applied spring force(s) $F_s$, which, as will be readily appreciated by one having ordinary skill in the art, are a function of the apparatus compression spring 26 (and, hence, spring constant thereof) that is employed.

Release of the suture 50 is accomplished in a similar manner as discussed above. However, in this embodiment, when the capture rod 30 is advanced from the static/retracted position shown in FIG. 5F, the distal end 31 of the capture rod 30 and, hence, tong member 60 advances out of the cannula lumen 41 to either the extended position shown in FIGS. 5B and 5C or the extended position shown in FIG. 5D to positively release and eject the suture 50 off the distal end 62 of the tong member 60 and, hence, apparatus 10.

As illustrated in FIGS. 5B-5D, the distal end of the ejection sleeve 45 is preferably disposed proximate the distal end 31 of the capture rod 30 to ensure the complete release and ejection of the suture 50 when the capture rod 30 is advanced from the static/retracted position.

Figure 6:
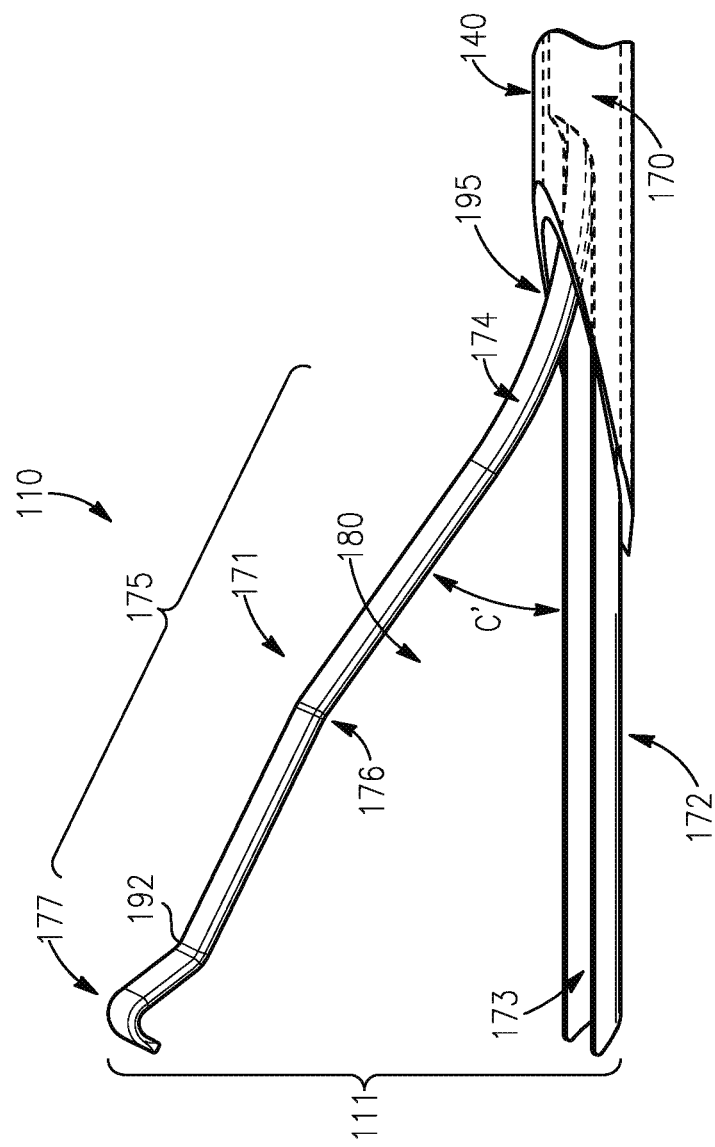
FIG. 6 is a partial perspective view of the capture finger and eject sleeve in the extended state, in accordance with the invention.

In an alternative embodiment, the capture rod or ejection sleeve 170 is secured to a flexible tong member 171. The ejection sleeve 170 could be a tubular shape with a lumen to receive a straight portion of the tong member. The ejection sleeve 170 has an extension 172 on the distal end, as shown in FIG. 6. When a tubular shape, the extension 172 has the tube wall removed on one side to create a trough 173 such that the tong member 171 can fit into the trough. The ejection sleeve 170 with a reduced profile at the distal extension 172 allows for both the extension 172 and the tong member 171 to retract within the lumen of the cannula.

Figure 7:
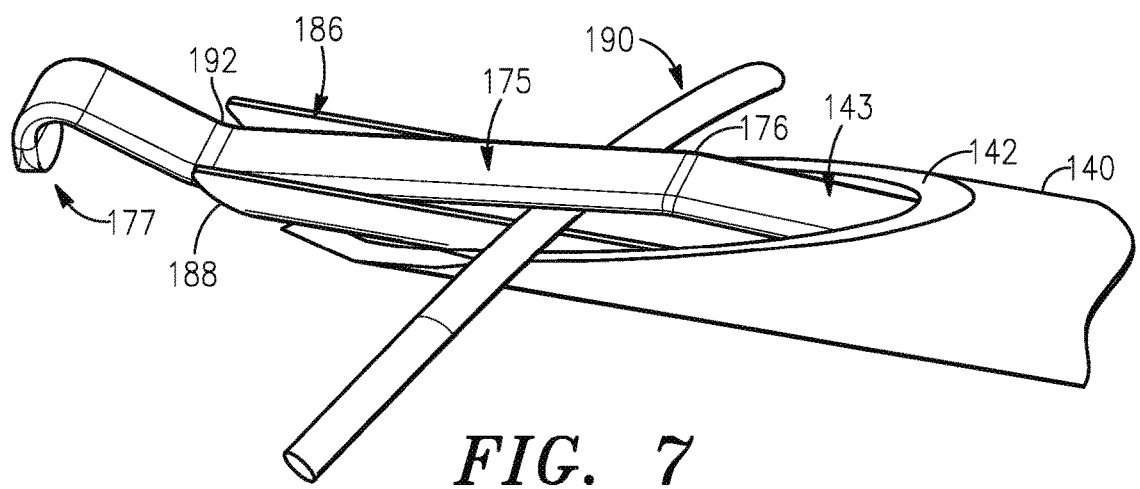
FIG. 7 is a partial perspective view of the capture finger and eject sleeve in the partially retracted state to begin capture of suture, in accordance with the invention.

As illustrated in FIGS. 6 and 7, the tong member 171 includes a primary bend 174, an elongated portion 175 separated by a second bend 176 and a distal end 177 that is configured to capture a suture thereon. According to the invention, the tong member 171 can comprise various configurations, i.e. cross sections. In the embodiment illustrated in FIG. 6-11C, the tong member 171 comprises a substantially rectangular ribbon member. The width of the ribbon tong member 171 provides optimum lateral clearance between the tong member 171 and the cannula 140.

According to the invention, the tong member distal end 171 can also comprise various configurations to facilitate capturing and seating a suture thereon. In some embodiments of the invention, such as illustrated in FIG. 6, the distal end 177 of the tong member 171 is configured in a hook shape, comprising a substantially linear region (or portion) 178 at an angle (denoted angle "D'") to the elongated portion 175 and a distal elongated portion 179 that is configured to form an apex angle (denoted angle "E"), As discussed below, preferably apex angle D' is less than approximately 75° to facilitate secure engagement of a suture on the tong member 171.

In some embodiments of the invention; particularly, wherein the tong member comprises a rectangular or band member, the distal end of the tong member can also comprise a hook region or section that is bent to a critical configuration or angle that prevents a suture from slipping underneath hook section when one leg of the suture is being pulled on axially.

Referring now to FIGS. 6 and 7, according to the invention, when the eject sleeve 170 is in a fully extended position or state, the elongated portion 175 of the tong member 171 and the distal extension 172 of the eject sleeve 170 form an aperture angle (denoted angle "C'").

Suture 190 can be placed in the primary aperture 180 for capture. Partial retraction of the tong member 171 and, hence, eject sleeve 170 effectively closes the primary apex 180 about the suture as illustrated in FIG. 7. Upon retraction of the eject sleeve 170 and, hence, flexible tong member 171 attached thereto (by either a spring force or manual manipulation at the handle), the tong member 171 contacts and is deflected by the inner edge 143 of the cannula 40, forcing the tong member 171 down toward the eject sleeve extension surface 186, whereby a suture engagement force between the tong member 171 and open eject sleeve extension surface 186 is provided that is sufficient to securely engage a captured suture between the tong member 171 and open eject sleeve extension surface 186.

Figure 9:
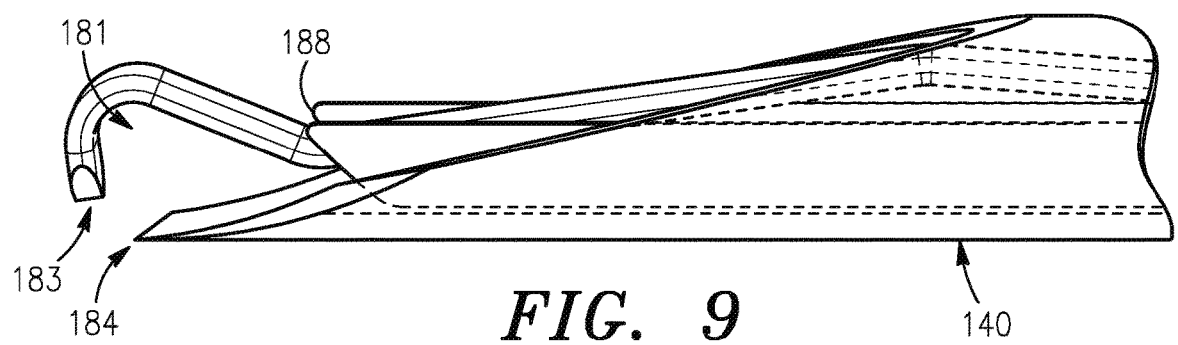
FIG. 9 is a partial perspective view of the capture finger and eject sleeve in the partially retracted state, in accordance with the invention.
Figure 10A:
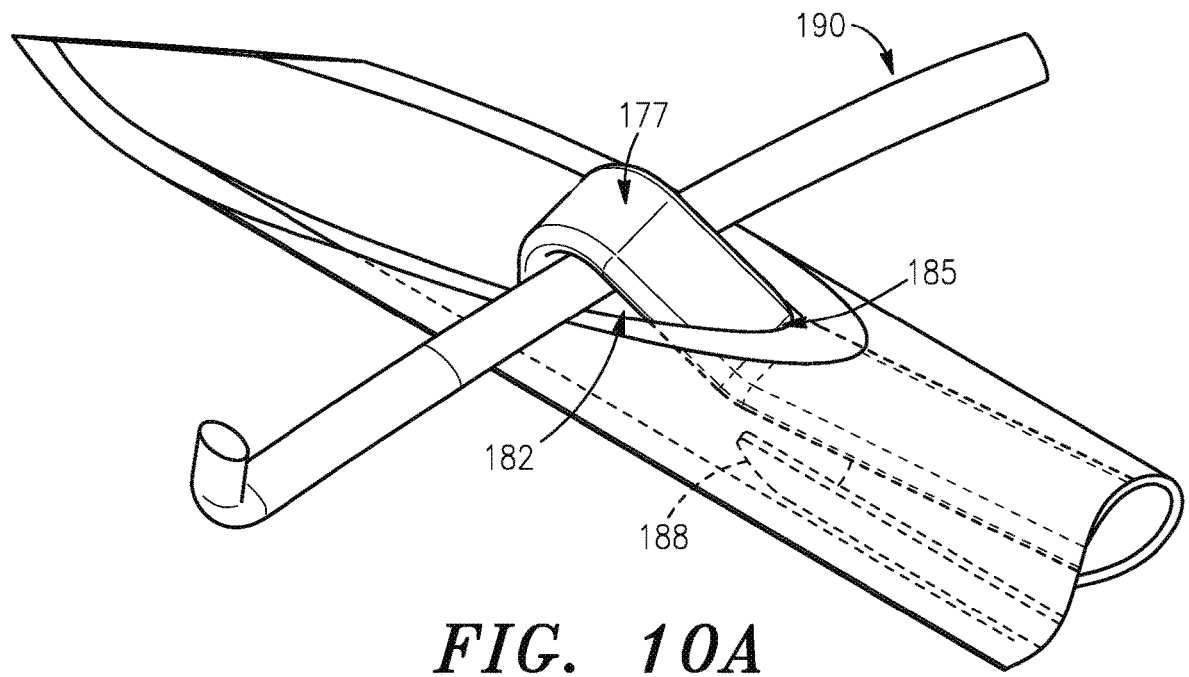
FIG. 10A is a partial perspective view of the capture finger and eject sleeve in the retracted state to fully capture suture, in accordance with the invention.

The hooked distal end 177 of the tong member 171 extends beyond the distal end of the ejection sleeve extension 172 as shown in FIG. 2. The hooked distal end 177 and cannula 140 create a "suture shuttle" area 81 when the primary apex 180 approaches zero (or the closed position) as illustrated in FIG. 9. Further retraction of the tong member 171 and, hence, eject sleeve, 170 causes the trapped suture 90 resting on the eject sleeve extension 172 to exert a force to flex the elongate section 175 of the tong member and allow the elongate section 175 to slide over the suture 90 until the suture gets captured in the "suture shuttle" area 181. As illustrated in FIG. 10A, continued retraction of the tong member 71 enables the hooked distal end 177 of the tong member 171 to draw the suture and wedge it between the hooked distal end 177 and the grind surface of the cannula 182.

Figure 8:
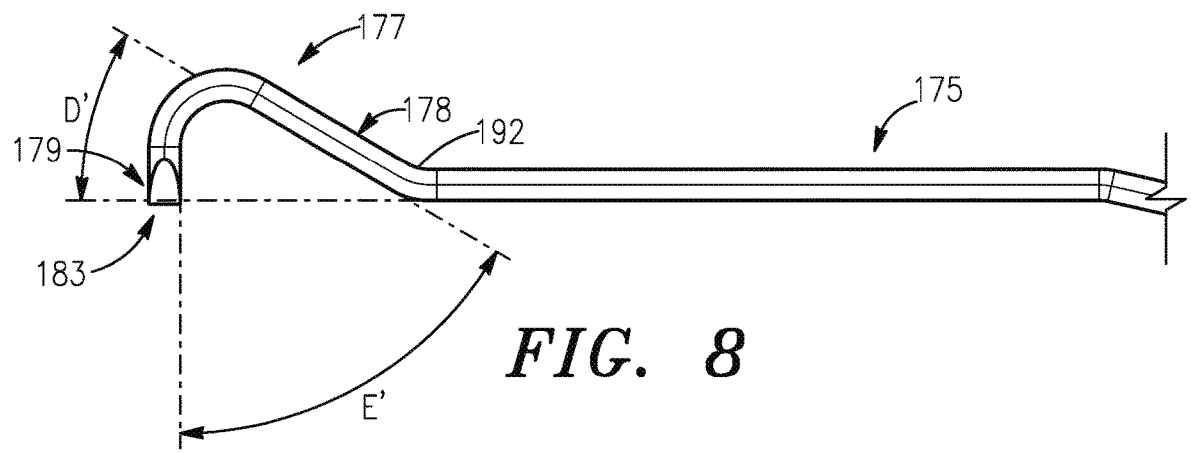
FIG. 8 is a side view of the capture finger, in accordance with the invention.

The hooked distal end has a formed inside angle E' that is 75 degrees or less and an adjacent angle D' of 20 degrees or greater. The tip 183 of the hooked distal end is also formed to terminate within 0.002+0.008/−0.012" of datum E' as shown in FIG. 8. FIG. 9 illustrates the tip 183 termination dimension is critical to assure the hooked distal end tip 183 does not catch against the tip 184 of the cannula 140 when being retracted, yet allows enough of a hook surface to adequately capture the suture 190.

Figure 10B:
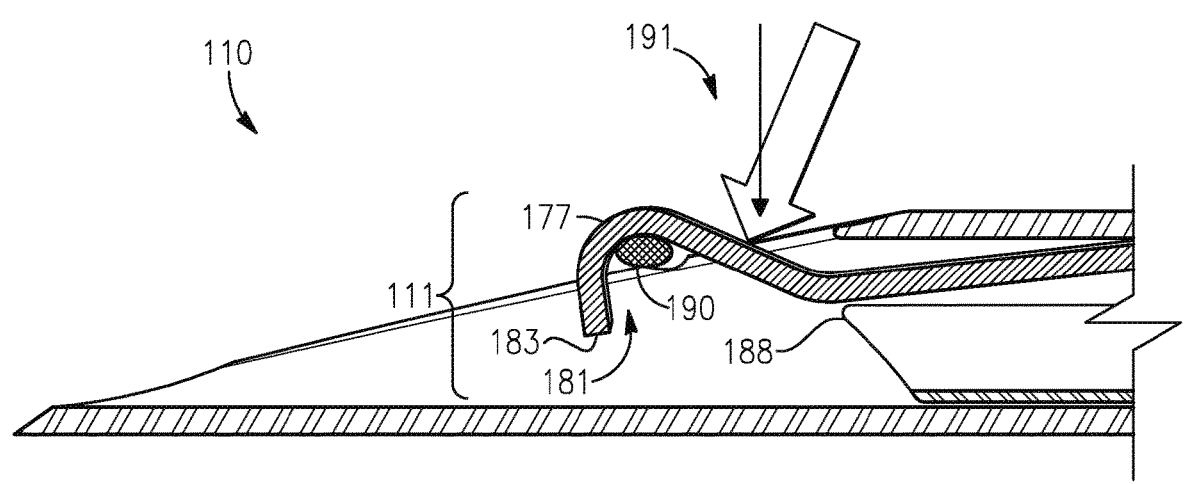
FIG. 10B is a partial sectional perspective view of the capture finger and eject sleeve in the retracted state to fully capture suture, in accordance with the invention.

As suture 190 is being pulled by the hook distal end 177 of the tong member 171 toward the heel 185 of the cannula, the suture 190 is wedged between the tong member 171 and the cannula grind surface 82. The axial retracting pull force on the tong member 171 is related to the Y direction force vector 191 being applied to collapse and/or shear the suture, as shown in FIG. 10B. Angle D' being greater than 20 degrees provides an angle engagement of the tong member 171 against the inner edge of the cannula 143 that results in a Y vector force substantially lower than if angle D' is small, i.e. less than 5 degrees. This relationship can prevent the suture from experiencing enough Y direction force to be flexed to the degree of collapsing and getting pulled inside the cannula. Preventing the suture from being flexed to the degree of collapsing lessens the potential of the suture from being damaged, i.e. severed. The suture is securely captured, yet not subject to damage.

Figure 11A:
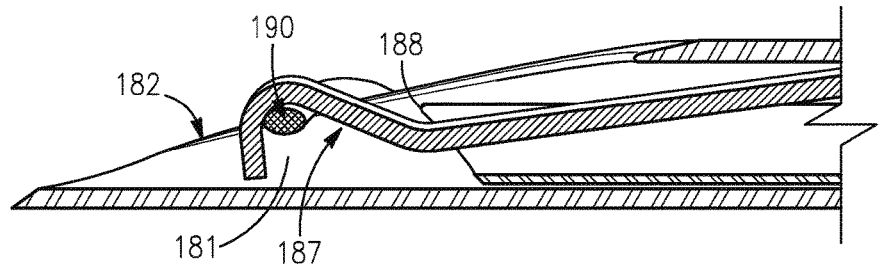
FIG. 11A is a partial sectional perspective view of the capture finger and eject sleeve in the partially extended state in process of releasing the suture, in accordance with the invention.
Figure 11B:
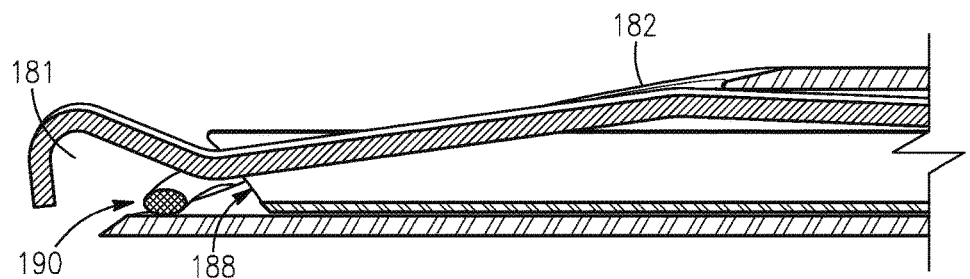
FIG. 11B is a partial sectional perspective view of the capture finger and eject sleeve in a further partially extended state beyond FIG. 11A in process of releasing the suture, in accordance with the invention.
Figure 11C:
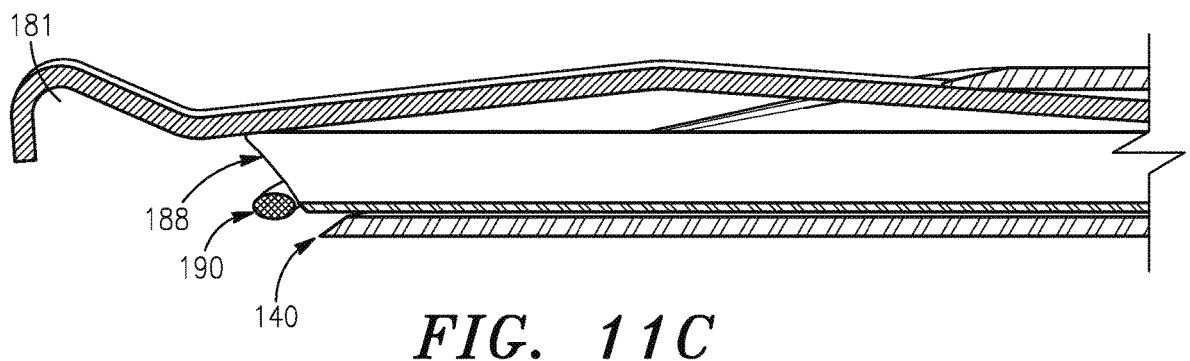
FIG. 11C is a partial sectional perspective view of the capture finger and eject sleeve in a further partially extended state beyond FIG. 11B in process of releasing the suture, in accordance with the invention.

To release the suture 190, the tong member 171 and, hence, eject sleeve 70 are advanced forward. The proximal surface 187 of the suture shuttle 181 of the tong member 171 pushes the suture down the bevel edge 182 of the cannula 140, as shown in FIG. 11A. As illustrated in FIG. 11B, as the suture 190 reaches the distal section of the cannula bevel edge 182, the suture 190 disengages from the suture shuttle 182 of the tong member 171, and the distal tip end 188 of the eject sleeve engages the suturel 190, continuing to push the suture 190 until it gets pushed off the end of the cannula 184, as shown in FIG. 11C).

This embodiment offers the significant advantages of
i. a large primary apex for ease of capturing suture,
ii. a large suture grasping/holding force without damaging suture,
iii. a positive release/ejection of the suture from the device.

Figure 12:
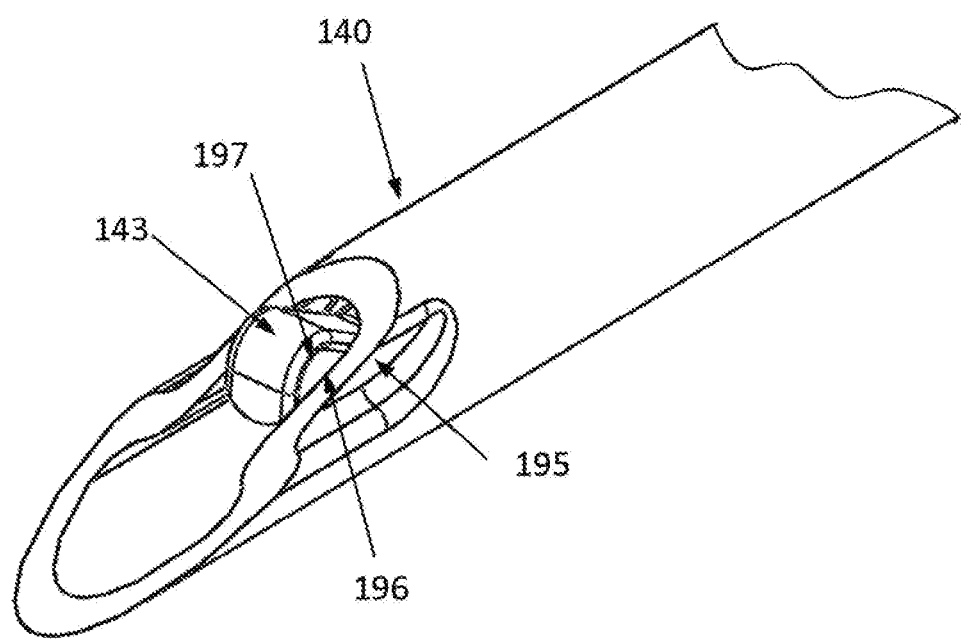
FIG. 12 is a partial perspective view of the capture finger partially extended state illustrating the lateral relationship to enhance suture retention when being captured by the capture finger.

In another embodiment, the suture passer could incorporate a formed feature 195 at the distal end of the cannula 140 as illustrated in FIG. 12. Both lateral sidewalls of the cannula are formed in to create straight edges 196 that provide a longitudinal edges parallel to the capture finger side edges 197. The gap between a cannula sidewall edge 196 and a capture finger sidewall edge kept to less than 0.010" to prevent #1 braided suture from collapsing and being pulled inside the cannula barrel. For other size sutures, the gap could be accommodated appropriately. In addition, minimizing the gap reduces the deformation the capture finger can create on a monofilament suture.

As will readily be appreciated by one having ordinary skill in the art, the present invention provides numerous advantages compared to prior art suture apparatus, systems and methods. Among the advantages are the following:

The provision of suture apparatus and methods that provide effective and accurate means for approximation, ligation and fixation of tissue.

The provision of suture apparatus and methods that can be effectively employed to approximate tissue in conjunction with endoscopic surgery procedures.

The provision of suture apparatus and methods that can be effectively employed to approximate tissue separated by means of an endosurgical trocar.

The provision of suture apparatus and methods that can be effectively employed to positively and, hence, effectively release suture from the apparatus.

The provision of suture apparatus and methods that can be effectively employed to provide to maximize suture retention capability.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A suture apparatus, comprising:
a handle comprising a housing;
an actuator comprising a longitudinal axis and a first proximal end and a first distal end;
a capture rod comprising a second proximal end and a second distal end, said capture rod second distal end comprising suture capture means for capturing and seating a first suture thereon, said suture capture means comprising a tong member, said first distal end of said actuator being engaged to said second proximal end of said capture rod to form an actuator-capture rod assembly;
an ejection member, said ejection member being in communication with said capture rod;
an elongated cannula shaft comprising a third proximal end and a third distal end, said elongated cannula shaft further comprising a lumen that is configured to receive said capture rod, said ejection member and said tong member therein; and
capture rod retraction means for retracting said actuator-capture rod assembly from an extended position to a retracted position, wherein
said housing comprises an internal region that is configured to receive and support said capture rod retraction means, said actuator first distal end and said actuator rod second proximal end therein, wherein said capture rod retraction means is in communication with said actuator,
said actuator-capture rod assembly and capture rod retraction means are positioned in said housing interior region, wherein, when an actuation force is applied to said actuator proximal end in a first direction, said actuator-capture rod assembly transitions from said retracted position to said extended position, wherein said suture capture means and said ejection member extend out of said lumen and said tong member is urged to transition from a restrained configuration in said lumen to an unrestrained configuration, wherein a suture capture opening is provided by said tong member and elongated cannula shaft, when said actuation force is released, said capture rod retraction means exerts a retraction force on said actuator-capture rod assembly to transition said actuator-capture rod assembly to said retracted position, said tong member comprises an elongated portion and a distal end portion, a first end of said elongated portion being connected to said capture rod distal end, said tong member distal end is configured and oriented with respect to said elongated portion to form a suture seat at a juncture of said elongated portion and said distal end, said suture seat being configured to capture and seat said first suture thereon, said tong member distal end having a proximal surface forming a portion of said suture seat, the proximal surface angled toward said ejection member such that, when said actuator-capture rod assembly transitions from said retracted position to said extended position, said proximal surface is configured to guide said first suture past said elongated cannula shaft and toward a distal end of said ejection member, where said distal end of said ejection member is configured to continue to move said first suture away from the elongated cannula shaft to eject said first suture.

2. The suture apparatus of claim 1, wherein when the actuation force is in the range of 0.5-4 lbs.

3. The suture apparatus of claim 1, wherein, when said first suture is captured and seated in said suture seat and said actuator-capture rod assembly transitions to said retracted position, said first suture is withdrawn into said cannula lumen.

4. The suture apparatus of claim 1, wherein said juncture of said elongated portion and said distal end comprises an angle less than 90°.

5. The suture apparatus of claim 1, wherein said first direction of said actuation force is parallel to said actuator longitudinal axis.

6. The suture apparatus of claim 1, wherein said first distal end of said actuator is engaged to said second proximal end of said capture rod by at least one guide pin, and wherein said housing further comprises at least one guide slot that is configured to receive, support and control travel of said at least one guide pin.

7. The suture apparatus of claim 1, wherein said capture rod retraction means comprises a compression spring.

8. The suture apparatus of claim 1, wherein said distal end of the elongated cannula shaft has a formed feature to minimize a gap between an inner wall of the elongated cannula shaft and a side edge of the tong member.

9. A suture apparatus, comprising:
a handle comprising a housing defining a housing interior;
a suture capture assembly positioned at least partially in the housing interior and movable between a biased fully retracted position and a fully extended position, the capture assembly comprising:
an actuator comprising a longitudinal axis and first proximal and distal ends,
a tong coupled to the actuator and comprising a distal hook with a hook distal end, and
an ejection member coupled to the actuator and comprising an ejection member distal end; and
an elongated cannula comprising a cannula shaft with a lumen configured to receive at least a portion of the capture assembly,
wherein when the actuator is moved in a distal direction, the suture capture assembly transitions from the biased fully retracted position to the fully extended position such that the tong and ejection member extend out of the lumen and form a suture capture opening,
wherein the hook distal end extends distally beyond the ejection member distal end when the suture capture assembly is in the biased fully retracted position, and
wherein said distal end of the elongated cannula has a formed feature to minimize a gap between an inner wall of the elongated cannula and a side edge of the tong, wherein
the gap sized to prevent a suture disposed in the suture capture opening to be retracted into the lumen.

10. The suture apparatus of claim 9, wherein:
the elongated cannula defines an X-axis;
the ejection member distal end and a tong distal end are vertically aligned along a Y-axis perpendicular to the X-axis when the suture capture assembly is in the fully extended position.

11. The suture apparatus of claim 10, wherein a juncture of the ejection member and the tong comprises an angle less than 90°.

12. The suture apparatus of claim 9, wherein the tong further comprises:
a first proximal bend directed away from the ejection member; and
a second inward bend directed toward the ejection member positioned between the first proximal bend and the hook.

13. The suture apparatus of claim 12, wherein the tong comprises:
an outward hook bend positioned at a base of the hook; and
a linear section between the second bend and the third bend.

14. The suture apparatus of claim 9, wherein:
the suture capture assembly is proximally biased to a captured retracted position when suture is positioned between the tong and the ejection member; and
the hook distal end extends distally beyond the ejection member distal end when the suture capture assembly is in the captured retracted position.

15. A suture apparatus, comprising:
a handle comprising a housing defining a housing interior;
a suture capture assembly positioned at least partially in the housing interior and movable between a fully retracted position and a fully extended position, the capture assembly comprising:
an actuator comprising a longitudinal axis and first proximal and distal ends,
a tong coupled to the actuator and comprising a distal hook with a hook distal end, and
an ejection member coupled to the actuator and comprising an ejection member distal end; and
an elongated cannula comprising a cannula shaft with a lumen configured to receive at least a portion of the capture assembly,
wherein when the actuator is moved in a distal direction, the suture capture assembly transitions from the fully retracted position to the fully extended position such that the tong and the ejection member extend out of the lumen and form a suture capture opening, wherein the hook distal end extends distally beyond the ejection member distal end when the suture capture assembly is in the fully retracted position, and wherein at least a distal end of both lateral sidewalls of the cannula shaft have straight edges that provide longitudinal edges parallel to side edges of the hook distal end of the tong.

16. The suture apparatus of claim 15, where a gap between the straight edges of the cannula shaft and the side edges of the hook distal end of the tong is sized to prevent a suture disposed in the suture capture opening to be retracted into the lumen.

17. The suture apparatus of claim 15, wherein:

the cannula shaft defines an X-axis;

the ejection member distal end and the tong distal end are vertically aligned along a Y-axis perpendicular to the X-axis when the suture capture assembly is in the fully extended position.

* * * * *